(12) United States Patent
Hasenoehrl et al.

(10) Patent No.: US 10,561,755 B2
(45) Date of Patent: *Feb. 18, 2020

(54) VOLATILE COMPOSITION DISPENSER WITH RETRACTABLE PUSH BUTTON

(71) Applicant: The Procter & Gamble Company, Cincinnati, OH (US)

(72) Inventors: Erik John Hasenoehrl, Loveland, OH (US); Rahul Vyas, Singapore (IN); Stefano Deflorian, Trento (IT); Walter Sordo, Trento (IT); Stefano Baldessari, Caldonazzo (IT); Ricard Tomas Vilarrasa, Trento (IT)

(73) Assignee: The Procter & Gamble Company, Cincinnati, OH (US)

( * ) Notice: Subject to any disclaimer, the term of this patent is extended or adjusted under 35 U.S.C. 154(b) by 150 days.

This patent is subject to a terminal disclaimer.

(21) Appl. No.: 15/582,834

(22) Filed: May 1, 2017

(65) Prior Publication Data

US 2017/0319732 A1 Nov. 9, 2017

Related U.S. Application Data

(60) Provisional application No. 62/330,869, filed on May 3, 2016.

(51) Int. Cl.
*A61L 9/12* (2006.01)
*B05B 12/00* (2018.01)
*A01M 1/20* (2006.01)

(52) U.S. Cl.
CPC ............. *A61L 9/12* (2013.01); *A01M 1/2044* (2013.01); *A61L 9/127* (2013.01);
(Continued)

(58) Field of Classification Search
CPC ........... A61L 9/12–127; A61L 2209/13; A61L 2209/131; A61L 2209/133;
(Continued)

(56) References Cited

U.S. PATENT DOCUMENTS

| | | | | |
|---|---|---|---|---|
| 4,526,320 A | * | 7/1985 | von Philipp | A01M 1/2044 239/34 |
| 5,875,968 A | * | 3/1999 | Miller | A61L 9/127 239/44 |

(Continued)

FOREIGN PATENT DOCUMENTS

| | | |
|---|---|---|
| WO | WO 98/16262 A1 | 4/1998 |
| WO | WO 2006/061802 A1 | 6/2006 |

OTHER PUBLICATIONS

All Office Actions for U.S. Appl. No. 15/582,828.
(Continued)

*Primary Examiner* — Cody J Lieuwen
(74) *Attorney, Agent, or Firm* — Abby A. Lopez

(57) ABSTRACT

There is a volatile composition dispenser comprising:
a housing comprising a rear frame having a frame opening
a push button movably disposed within the frame opening; and
a cartridge aligned with the push button, the cartridge comprising a container having an orifice and containing a volatile composition, a rupturable substrate sealably attached to and covering the orifice, and rupture elements adjacent the rupturable substrate; and a resilient member aligned with the push button and the rupture elements wherein upon receiving a pressure on the push button, said resilient member moves the rupture elements into a first position in which the rupture elements engage with the rupturable substrate and wherein upon removing the pressure from the push button, said resilient member exerts a force on the push button and (Continued)

moves the rupture elements into a second position in which the rupture elements are not engaged with the rupturable substrate.

11 Claims, 10 Drawing Sheets

(52) U.S. Cl.
CPC ..... *B05B 12/0022* (2018.08); *A61L 2209/131* (2013.01); *A61L 2209/133* (2013.01)

(58) Field of Classification Search
CPC ........... A61L 2209/134; A01M 1/2044; A01M 1/2055; B05B 12/002–0026
USPC .......................................... 239/34–60; 74/56
See application file for complete search history.

(56) References Cited

U.S. PATENT DOCUMENTS

| | | | | |
|---|---|---|---|---|
| 8,622,209 | B2* | 1/2014 | Isaac | B65D 81/32 206/222 |
| 8,740,110 | B2 | 6/2014 | Gruenbacher et al. | |
| 8,931,711 | B2 | 1/2015 | Gruenbacher et al. | |
| 9,015,989 | B1* | 4/2015 | Zeamer | A01M 1/2005 239/37 |
| 9,439,993 | B2 | 9/2016 | Gruenbacher et al. | |
| 2006/0191189 | A1* | 8/2006 | Mayo | A01M 1/2005 43/131 |
| 2010/0310429 | A1* | 12/2010 | Kanner | A61L 9/18 422/113 |
| 2010/0314461 | A1* | 12/2010 | Gruenbacher | A61L 9/12 239/6 |
| 2011/0180621 | A1 | 7/2011 | Gruenbacher et al. | |
| 2012/0312706 | A1* | 12/2012 | Isaac | B65D 81/32 206/222 |
| 2014/0103136 | A1* | 4/2014 | Sidawi | A61L 9/127 239/44 |
| 2015/0060565 | A1 | 3/2015 | Furner | |
| 2016/0354505 | A1 | 12/2016 | Gruenbacher et al. | |
| 2017/0043047 | A1 | 2/2017 | Beck et al. | |

OTHER PUBLICATIONS

All Office Actions for U.S. Appl. No. 15/582,841.
All Office Actions for U.S. Appl. No. 15/582,849.
PCT Search Report PCT/US2017/030713; dated Jul. 26, 2017; 13 Pages.
PCT Search Report PCT/US2017/030715; dated Jul. 26, 2017; 14 Pages.
PCT Search Report PCT/US2017/030716; dated Jul. 20, 2017; 13 Pages.
PCT Search Report PCT/US2017/030717; dated Sep. 11, 2017; 15 Pages.
U.S. Appl. No. 15/582,828, filed May 1, 2017, Hasenoehrl, et al.
U.S. Appl. No. 15/582,841, filed May 1, 2017, Hu, et al.
U.S. Appl. No. 15/582,849, filed May 1, 2017, Deflorian, et al.

* cited by examiner

VOLATILE COMPOSITION DISPENSER WITH RETRACTABLE PUSH BUTTON

FIELD OF THE INVENTION

The invention relates to volatile material product packaging and in particular to a volatile composition cartridge with a rupture mechanism configured to provide a deflection within the cartridge when the volatile composition cartridge is pressed. More particularly, the invention relates to a volatile composition dispenser for delivering a volatile material comprising the volatile composition cartridge and a push-button housing for the volatile composition cartridge wherein the push-button is retractable and a method of attaching the volatile composition dispenser to the push-button housing for delivering a volatile material.

BACKGROUND OF THE INVENTION

Systems for delivering volatile materials to the atmosphere are well known in the art. Such systems include insect repellents, air fresheners, malodor removal agents, or the like, and function by evaporating a volatile material into a space to deliver a variety of benefits such as air freshening or malodor removal.

PCT Publication No. WO 98/16262 (hereinafter, "WO98/16262") describes a disposable air freshener dispenser device having a push-button actuator which can be manually operated to initiate the dispensing of air freshener composition into the atmosphere. The device of WO98/16262 has an air freshener medium within a container, and a push button actuator which can be manually operated to rupture a foil covering the container for initiating the dispensing of the air freshener into the atmosphere. However, after the foil is ruptured, the push button actuator stays on the openings within the foil and obstructs the path for dispensing the air freshener. Therefore, there exists a need for a push button that enables the foil to be ruptured without obstructing a dispensing of the air freshener.

SUMMARY OF THE INVENTION

In order to address the aforementioned needs, the present invention presents a volatile composition dispenser comprising:
  a housing comprising a rear frame having a frame opening;
  a push button movably disposed within the frame opening; and
  a cartridge aligned with the push button, the cartridge comprising a container having an orifice and containing a volatile composition, a rupturable substrate sealably attached to and covering the orifice, and rupture elements adjacent the rupturable substrate; and a resilient member aligned with the push button and the rupture elements wherein upon receiving a pressure on the push button, said resilient member moves the rupture elements into a first position in which the rupture elements engage with the rupturable substrate and wherein upon removing the pressure from the push button, said resilient member exerts a force on the push button and moves the rupture elements into a second position in which the rupture elements are not engaged with the rupturable substrate.

By having the resilient member and the push button being movably disposed within the frame opening, the rupture elements and the button may be moved away from punctured holes in the rupturable substrate after rupturing, such that the volatile composition may be dispensed in an unobstructed manner.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

DETAILED DESCRIPTION OF THE INVENTION

The present invention relates to a volatile composition dispenser for the delivery of a volatile material to the atmosphere. The dispenser is suitable for purposes of providing fragrances, air fresheners, deodorizers, odor eliminators, malodor counteractants, insecticides, insect repellants, medicinal substances, disinfectants, sanitizers, mood enhancers, aromatherapy aids, or for any other purpose using a volatile material or a volatile composition that acts to condition, modify, or otherwise change the atmosphere or the environment. For the purposes of illustrating the present invention in detail, but without intending to limit the scope of the invention, the invention will be described in a volatile composition dispenser for delivering a liquid composition containing perfume, perfume ingredients and or perfume raw materials.

Figure 1:
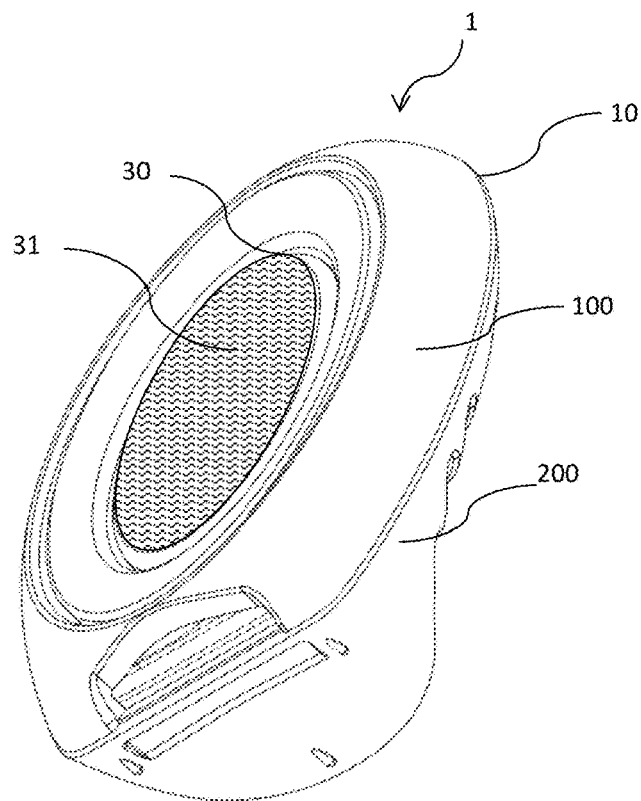
FIG. 1 is a front perspective view of a volatile composition dispenser according to an embodiment.
Figure 2:
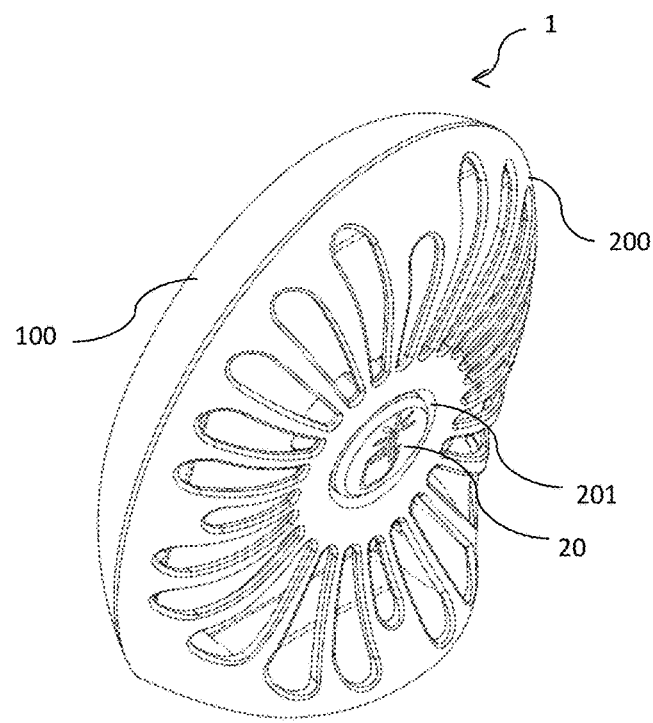
FIG. 2 is a rear perspective view of the volatile composition dispenser shown in FIG. 1.

FIG. 1 shows a front perspective view of an embodiment of a volatile composition dispenser 1 (hereinafter "dispenser") according to the present invention and FIG. 2 shows a rear perspective view of the dispenser 1. The dispenser 1 comprises a housing 10 having a front cover 100 and a rear frame 200, the front cover 100 and the rear frame 200 defining an interior space. The rear frame 200 is provided with a frame opening 201 (hereinafter "opening") located substantially in the centre of the rear frame 200. A push button 20 (hereinafter "button") is disposed within the opening 201 and is movable with respect to the rear frame 200 for enabling a user to activate the dispenser 1. A cartridge 30 containing a volatile composition 31 is located within the housing 10.

Figure 3:
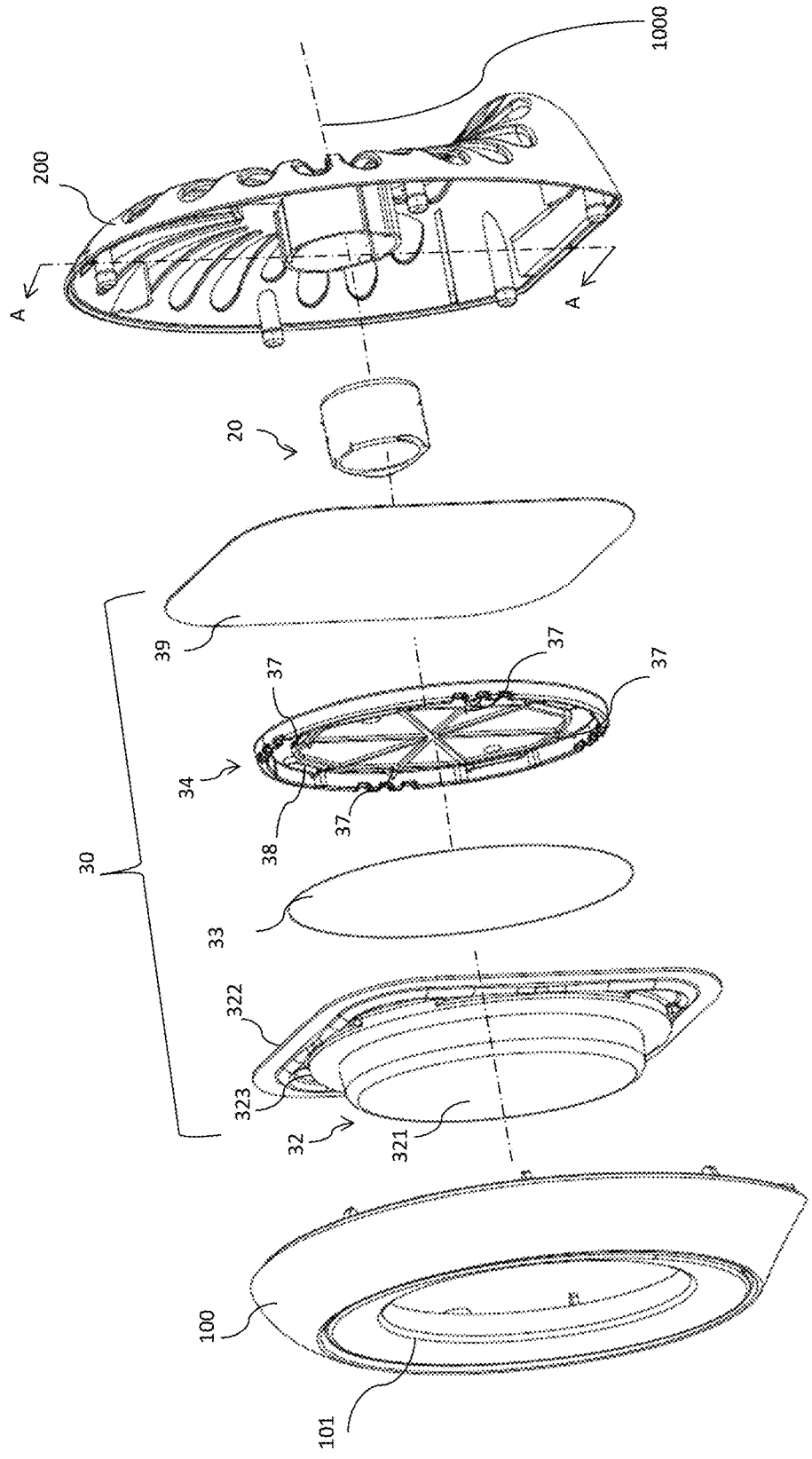
FIG. 3 is a side perspective exploded view of the volatile composition dispenser shown in FIG. 1.

FIG. 3 shows internal components of the dispenser 1. The front cover 100 comprises a window 101 configured for displaying the cartridge 30. The cartridge 30 comprises a container 32 having an orifice 321, within which the volatile composition 31 (as shown in FIG. 1) is stored. A rupturable substrate 33 is sealably attached to and covers the orifice 321 defining a reservoir to prevent the volatile composition 31 from being released until the dispenser 1 is activated. The rupturable substrate 33 may be ruptured to release the volatile composition 31 by actuating a rupture mechanism 34 positioned adjacent to the rupturable substrate 33. The rupture mechanism 34 comprises a movable member 35 movably attached to an outer frame 36 by a resilient member 38. The resilient member 38 may be formed of one or more springs 38. One or more rupture elements 37 are arranged within the rupture mechanism 34 to puncture holes in the rupturable substrate 33. The rupture element 37 may be a pin. The cartridge 30 may comprise a membrane 39 located on the exterior of the cartridge 30. The membrane 39 may be sealably attached to a flange 322 located at a periphery 323 of the container 32. The membrane 39 encloses the container 32, the volatile composition 31, the rupturable substrate 33, and the rupture mechanism 34. The membrane 39 may be configured to flex when a pressure or an actuation force is applied on the membrane 39.

Figure 7A:
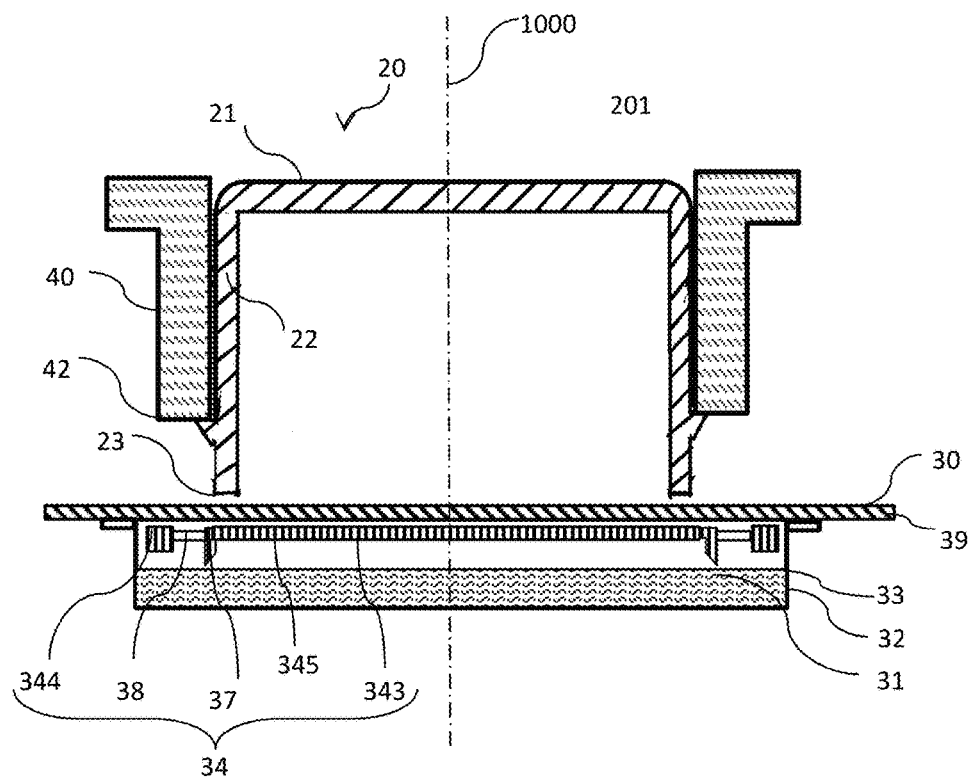
FIGS. 7A to 7C are schematic drawings which depict the movement of the button of FIG. 5 within the rear frame of FIG. 4.
Figure 7B:
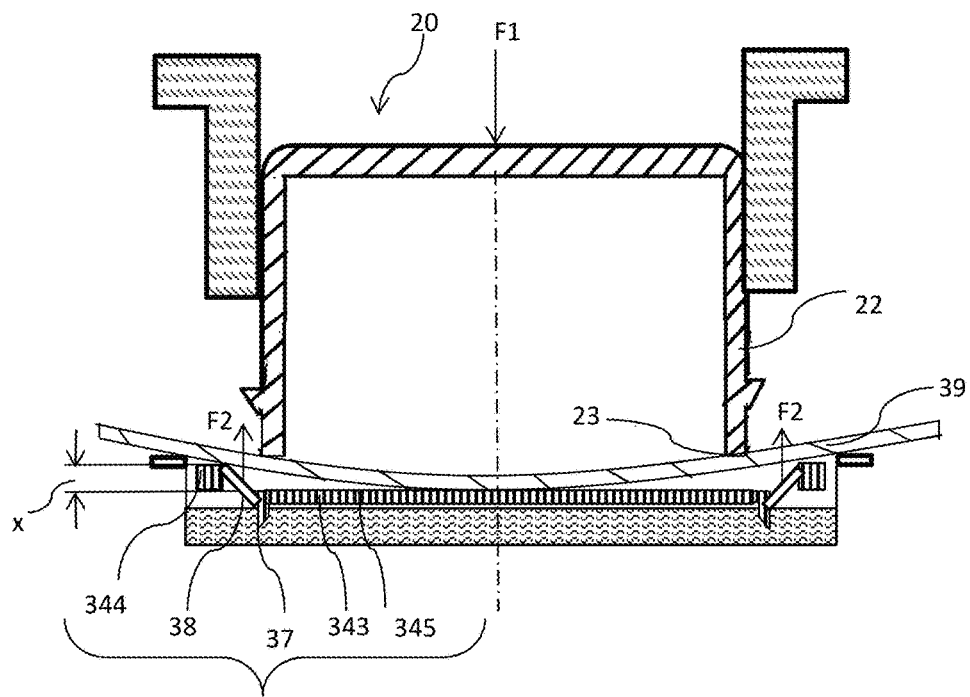

To activate the dispenser 1, a user depresses the button 20 until it makes contact with the rupture mechanism 34 (through the deflection of the membrane 39 as shown in FIG. 7B), and the rupture elements 37 on the rupture mechanism 34 pierce the rupturable substrate 33. Once the rupturable substrate 33 is pierced, the volatile composition 31 flows out of the container 32, wets the membrane 39 and is then delivered to the atmosphere surroundings through evaporation from the membrane 39.

The button 20 and the rear frame 200 are configured to enable efficient and controlled rupturing of the rupturable substrate 33 in the cartridge 30 while additionally providing a tactile and intuitive user experience to the user for activating the dispenser 1.

Figure 4:
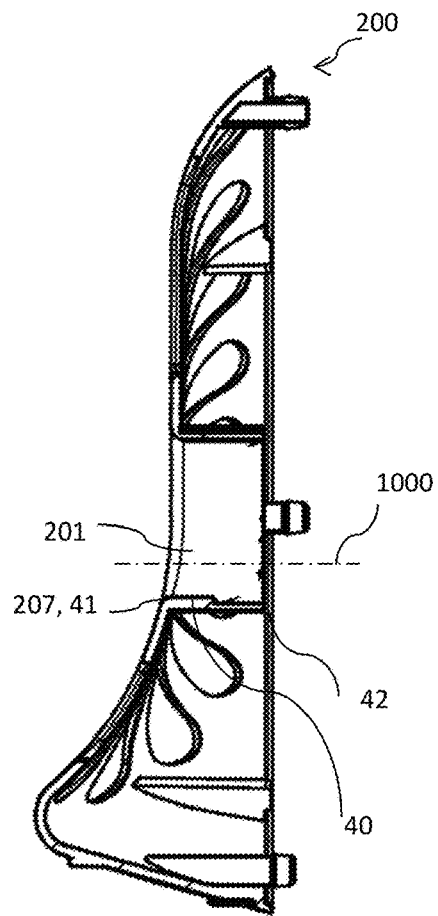
FIG. 4 is a side section view of a rear frame for a volatile composition dispenser according to an embodiment.

FIG. 4 shows a side section view A-A of the rear frame 200. An inner wall 40 is provided at a periphery 207 of the opening 201 and extends into the housing 10 from the interior of the rear frame 200. The inner wall 40 has a proximal end 41 flush with the periphery 207 of the opening 201, and a distal end 42 protruding into the housing 10. In the embodiment shown in FIG. 4, the inner wall 40 is solid and tubular in shape. However, the inner wall 40 may take some other shape such as for example a square cross section or a rectangular cross section. The inner wall 40 may be substantially cylindrical and comprise a continuous wall, or a segmented wall such as for example, a lattice structure or multiple elongate struts connected to one another. The inner wall 40 may define an extension of the opening 201 into the housing 10 with a central longitudinal axis 1000 running through the centre of the opening 201 and along which the button 20 can be depressed. Alternatively, the inner wall 40 may protrude out of the housing 10 such that the inner wall 40 defines an extension of the opening 201 out of the housing 10. Accordingly, the distal end 42 may be flush with the periphery 207 of the opening 201 and the proximal end 41 may protrude out of the housing 10.

Figure 5:
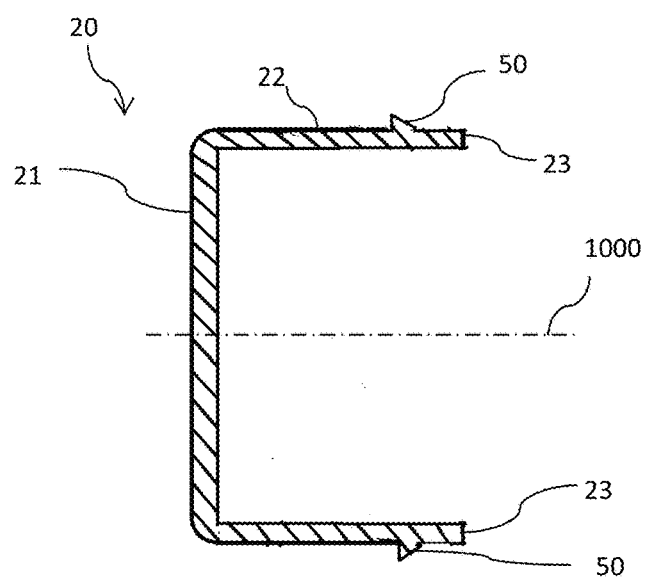
FIG. 5 is a front section view of a push button for a volatile composition dispenser according to an embodiment.
Figure 14A:
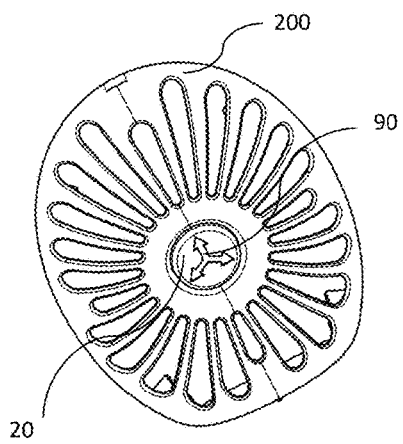
FIG. 14A is a rear perspective view of a volatile composition dispenser with a push button flush with a periphery of an opening in a rear frame in a first position before activation.
Figure 15A:
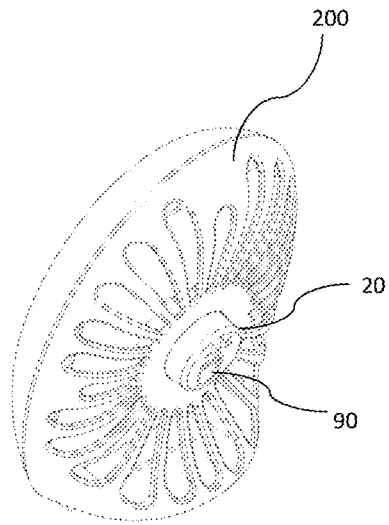
FIG. 15A is a rear perspective view of a volatile composition dispenser with a button positioned above a periphery of an opening in a rear frame in a first position before activation.

FIG. 5 is a front section view of the button 20 configured to fit and to move within the opening 201 of the rear frame 200. The button 20 comprises a top 21 and a button body 22 extending from the top 21 into the housing 10. In an embodiment, the top 21 is located in line with the periphery 207 of the opening 201 when the button 20 is in an "at rest" position (see for example FIG. 14A). Alternatively, the top 21 of the button 20 may protrude out of the opening 201 when "at rest" (see for example. FIG. 15A). The button body 22 extends substantially in parallel to the inner wall 40. Therefore the button body 22 may also have a tubular shape. One or more protrusions 50 extend from the button body 22 to define snap fits for assembling the button 20 to the inner wall 40.

Figure 6A:
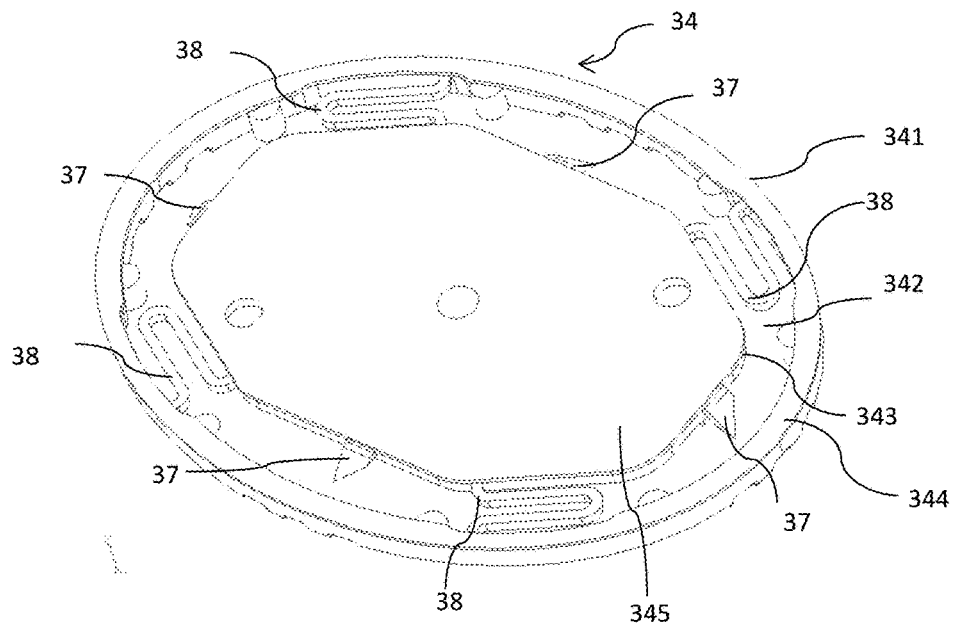
FIG. 6A is a front perspective view of a rupture frame for a volatile composition cartridge according to an embodiment.
Figure 6B:
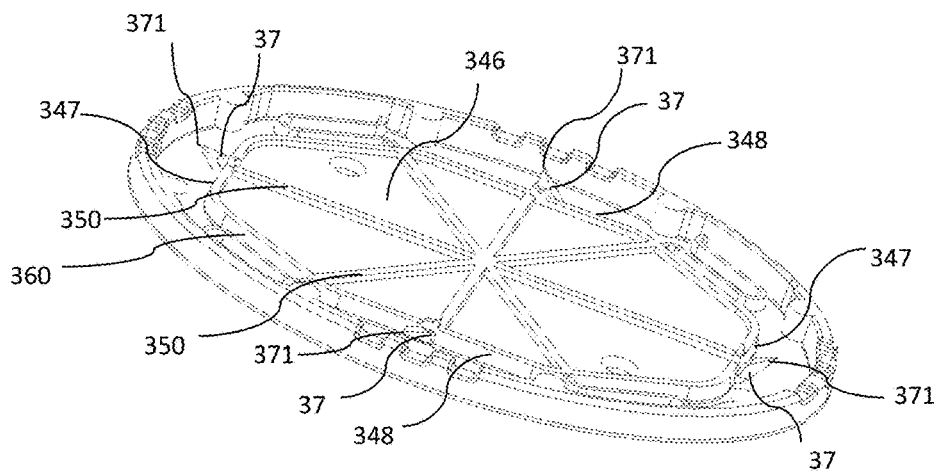
FIG. 6B is a rear perspective view of the rupture frame of FIG. 6A.

Referring to FIGS. 6A and 6B, the rupture mechanism 34 has a wall 341 which comprises a groove 342 extending circumferentially within the wall 341 to define a center portion 343 inside the groove 342 and an outer portion 344 outside the groove 342. The center portion 343 comprises a substantially planar first surface 345 and a second surface 346 opposite the first surface 345. The center portion 343 (hereinafter "movable portion") is movable relative to the outer portion 344 through flexing of the resilient member 38 when a force is received on the first surface 345 during actuation of the button 20. The resilient member 38 may be a spring resiliently connecting the outer portion 344 to the movable portion 343.

As shown in FIG. 6B, the rupture elements 37 are spaced apart on the center portion 343 and extend from at least two sides 347 orthogonal to the first surface 345 wherein each rupture element 37 comprises a tip 371 for puncturing the rupturable substrate 33. A first pair of rupture elements 37 is disposed on first opposing sides 347 of the movable portion 343 to enable rupturing of the substrate 33. A second pair of rupture elements 37 may be disposed on second opposing sides 348 different from the first opposing sides 347 to enable use of the cartridge 30 in different orientations. The position of the rupture elements 37 are configured to puncture at a hole at one side of the rupturable substrate 33 to allow air to enter the container 32 and another hole at an opposing side to drain the volatile composition from the container 32.

For example, in a vertical orientation of the cartridge 30 as shown in FIG. 1, the first pair of rupture elements 37 positioned on the first opposing sides 347 enable puncturing at least a pair of opposing holes in the rupturable substrate 33 which generates a pressure difference between the container interior and the container exterior. This pressure difference enables the volatile composition to be drained from one of the punctured holes located at the lower end of the rupturable substrate 33 as air enters the container 32 through the other punctured hole at the upper end of the rupturable substrate 33.

Further, the movable portion 343 may comprise one or more elongate ribs 350 arranged to increase rigidity or stiffness of the movable portion 343 such that the movable portion 343 may be moved within a plane substantially parallel to first surface 345 when engaged with the button 20. For example, as shown in FIG. 6B, the elongate ribs 350 may protrude from the second surface 346 and extend from each side 360 adjacent to the resilient member 38 and converge at the center of the movable portion 343. The elongate ribs 350 may also protrude from the second surface 346 and extend from the first and second opposing sides 347, 348 of the movable portion 343 and converge at the center.

Figure 6C:
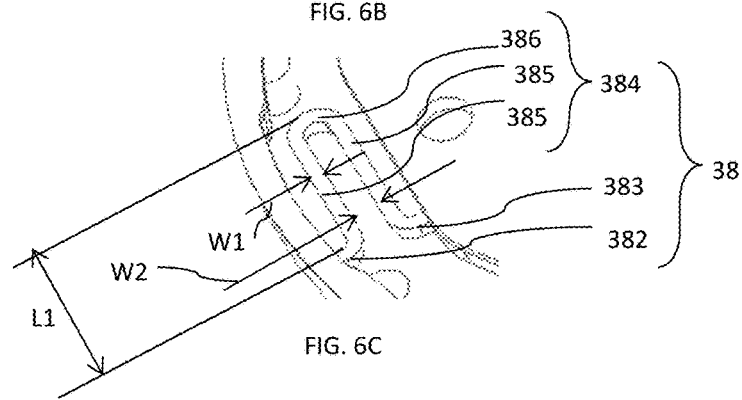
FIG. 6C is a detailed view of a resilient member for the rupture frame of FIG. 6A.

FIG. 6C is a detailed view of the resilient member 38 as shown in FIG. 6A. As shown in FIG. 6C, the resilient member 38 may be a spring or a parallel spring system. The spring may be a beam or a torsional member. In an embodiment, the resilient member 38 is a torsional may comprise a first arm 382 attached to the outer portion 344 and a second arm 383 attached to the center portion 343, and an elongate channel member 384 extending between the first and second arms 382, 383. The elongate channel member 384 comprises a first width, W1 and a channel width, W2 substantially parallel to the first surface 345 of the movable portion 343. The elongate channel member 384 may comprises a channel length, L greater than the channel width, W2. In an embodiment, the elongate channel member 384 comprises two side beams 385 and a bottom beam 386 arranged to form a substantially U-shape.

Figure 7C:
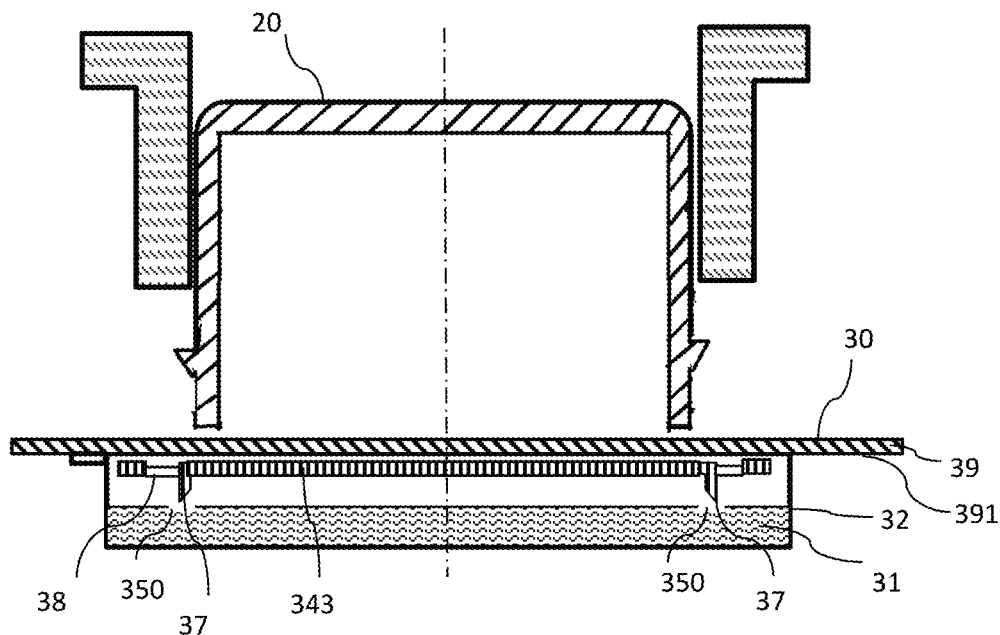

FIG. 7A is a cross-sectional view of the button 20 mounted within the rear frame 200 wherein the button 20 is in an "at rest" position. FIGS. 7B and 7C are cross-sectional views depicting the movement of the button 20 between the "at rest" position to a post-activation position. The button 20 is configured to move linearly with respect to the rear frame 200, i.e., a straight push button that moves in a direction generally parallel to the longitudinal axis 1000 of the frame opening 201 upon depression of the button 20.

In the "at rest" position, a distal end 23 of the button body 22 sits proximal to and adjacent the distal end 42 of the inner wall 40 and the resilient member 38 is in an equilibrium position. In the equilibrium position, the resilient member 38 is substantially parallel to the first surface 345 of the movable portion 343 and rupture elements 37 do not engage the rupturable substrate 33 of the cartridge 30. The resilient member 38 may be aligned with the push button 20 in the "at rest" position in which the resilient member 38 is in an unbiased condition. Further, the resilient member 38 may be aligned with the push button 20 and the rupture elements 37 to, upon receiving a pressure on the push button 20, store energy and move the rupture elements 37 into a first position as shown in FIG. 7B.

Figure 13A:
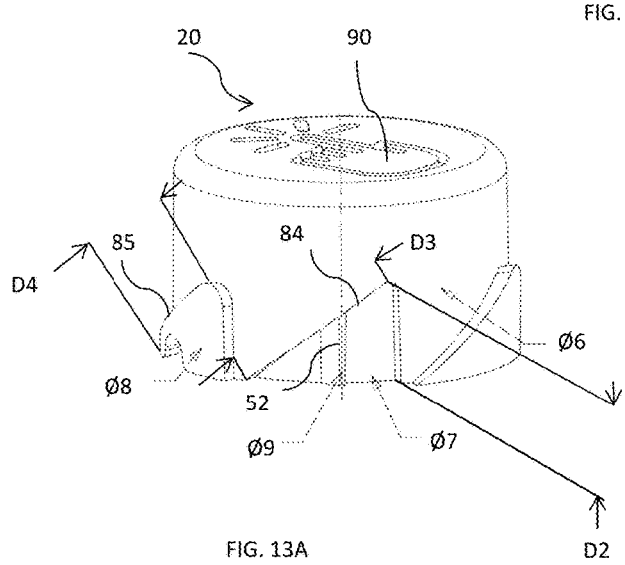
FIG. 13A is a perspective view of a cam guide on a push button for a volatile composition dispenser.
Figure 13B:
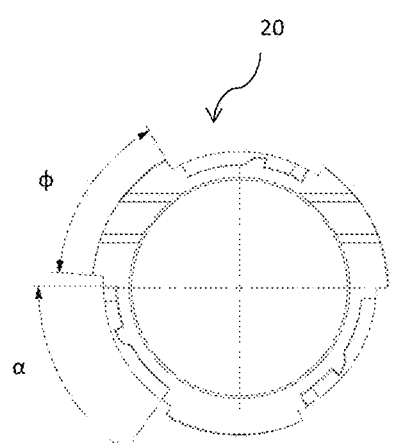
FIG. 13B is a bottom view of the push button of FIG. 13A.
Figure 14B:
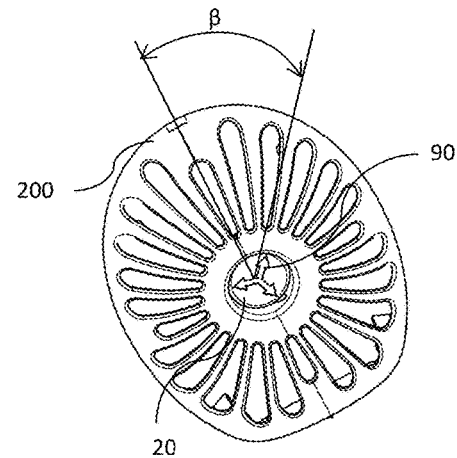
FIG. 14B is a rear perspective view of the push button of FIG. 14A in a second position after activation.

Referring to FIG. 7B, when the button 20 is pressed with a force F1 in a direction along the longitudinal axis 1000 and moves into the interior of the housing 10 (as shown in FIG. 13B, FIG. 14B), a pressure is applied on the membrane 39 and transferred to the movable portion 343 of the rupture mechanism 34. As the movable portion 343 moves under the pressure towards the rupturable substrate 33, the resilient member 38 deflects and twists about a plane parallel to the movable portion 343 such that the resilient member 38 is not parallel to the first surface 345. The twisting of the resilient member 38 allows movement of the movable portion 343 and consequently the rupture elements 37 on the movable portion 343 are moved into engagement with the rupturable substrate 33 and puncture holes 350 in the substrate 33 as shown in FIG. 7C. In FIG. 7B, energy, U is stored in the resilient member 38 as a result of the twisting of the resilient member 38 which may be defined as $$U = \tfrac{1}{2} k \theta^2 \text{ (Joules)}$$

wherein
k=spring constant of the resilient member and
θ=angle of twist of the resilient member from its equilibrium position (radians).

Referring to FIGS. 7B and 7C, the puncturing of holes 350 in the rupturable substrate 33 of the cartridge 30 by the rupture elements 37 break the seal and air enters the container 32 creating an air pressure inside the container 32. The air pressure initiates a release of the volatile composition 31 through the holes 350 in the substrate 33 and the volatile composition 31 impregnates a surface 391 of the membrane 39.

The resilient member 38 may also configured to, upon removing the pressure from the push button 20, exert a force such as a spring force on the push button 20 and move the rupture elements 37 into a second position in which the rupture elements 37 are not engaged with the rupturable substrate 33. Specifically, when F1 is removed from the button 20, i.e., F1 is removed from and is not acting on the button 20, the stored energy, U of the resilient member 38 is transformed into kinetic energy and exerts a spring force F2 or a torque, T in the opposite direction to the force F1 as shown in FIG. 7B and returns or springs back to the equilibrium position as shown in FIG. 7C. Consequently, the movable portion 343 is moved back to the equilibrium position through the resilient member 38 and the rupture elements 37 are moved out of the holes 350. A resultant force on the button 20 is the spring force due to the displacement x or the angle of twist θ and the resultant force moves the button 20 in the opposite direction away from the activation position of FIG. 7B. A magnitude of the force F2 made by the resilient member 38 may be less than or equal to a force required to return the button 20 to the at rest position (FIG. 7A). As a result, the button 20 may be moved away from the activation position (FIG. 7B) to the at rest position (FIG. 7A) or to a post-activation position (FIG. 7C) intermediate the at rest position and the activation position.

A technical effect of the resilient member 38 is that the button 20 being movable away from the activation position is to prevent the rupture elements 37 from staying in the holes 350 to permit draining of the volatile composition 31 from the container 32 through the holes 350 in the rupturable substrate 33.

Figure 15B:
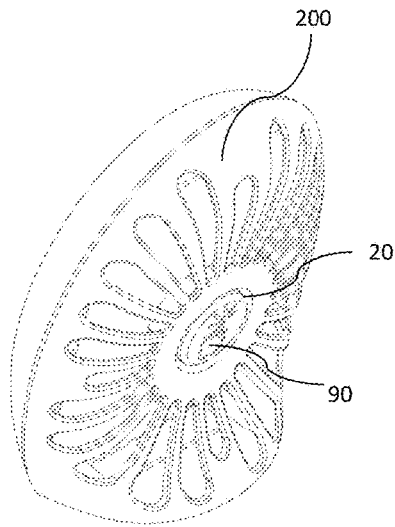
FIG. 15B is a rear perspective view of the push button of FIG. 14A in a second position after activation.

Another technical effect is to enable the button 20 to be in a post-activation position (FIG. 14B, FIG. 15B) different from the at rest position (FIG. 14A, FIG. 15A) after activation of the dispenser 1 thereby sending a signal to the consumer that the dispenser 1 is activated.

Figure 8:
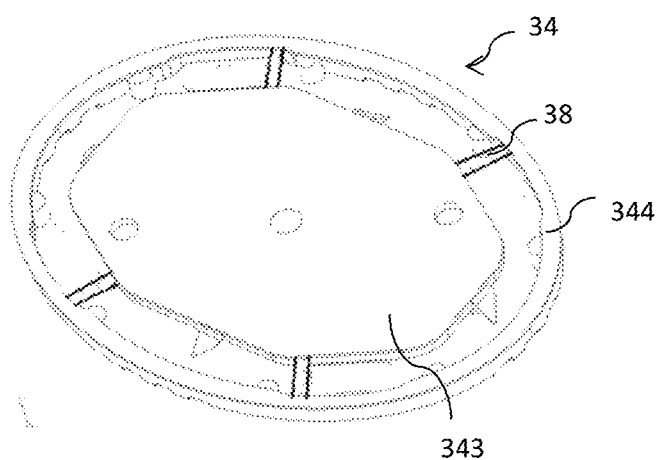
FIG. 8 is an alternative embodiment of a rupture frame for a volatile composition cartridge.

FIG. 8 shows a resilient member 38 for the rupture frame 34. The resilient member 38 may be an elongate spring beam arranged between the outer portion 344 and the movable portion 343. The resilient member 38 may have a linear force-relationship, following Hooke's law, F=kx, wherein F is the spring force of the spring measured in newtons (N), k is the stiffness of the spring measured in newtons/meter (N/m) and x is the displacement along the longitudinal direction 1000 (see FIG. 7B).

Depending on the design of the resilient member 38, the stiffness, k of the resilient member 38 may be configured to provide a desired displacement, x along the longitudinal direction 1000 or a desired angle of twist in the resilient member 38.

Figure 9A:
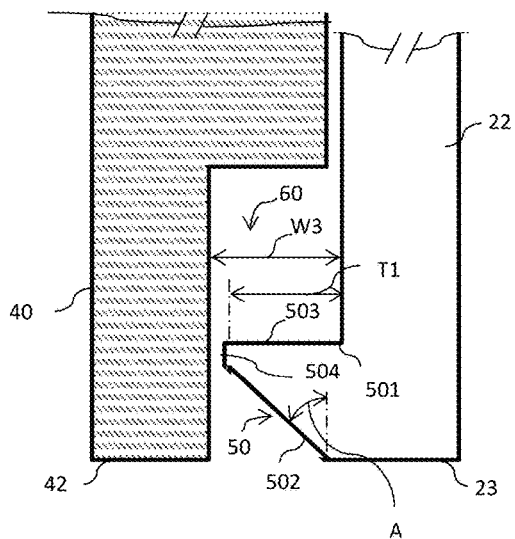
FIGS. 9A and 9B are detailed side section views showing different configurations of a protrusion for the dispenser.
Figure 9B:
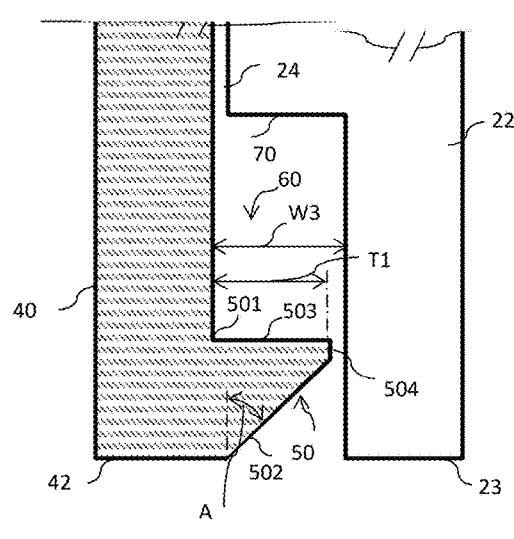

FIGS. 9A and 9B are schematic views of the button 20 within the inner wall 40 in the at rest position. There may be a gap 60 between the button body 22 and the inner wall 40 wherein one or more protrusions 50 are located at the distal end 42 of the inner wall 40 (FIG. 9A) or the distal end 23 of the button body 22 (FIG. 9B) and arranged within the gap 60. The size of the gap 60 may be uniform and constant along the longitudinal direction (length) of the button body 22 or the button 20.

The gap 60 comprises a first gap width (W3) between the base 501 of the protrusion 50 on the inner wall 40 or the button body 22. In an embodiment, wherein the axes of the inner wall 40 and the button body 22 are coaxial and are substantially cylindrical, the first gap width, W3 of the gap 60 is defined as $$W3=(\emptyset_1-\emptyset_2)/2$$

wherein
$\emptyset_1$=inner diameter of the inner wall (mm) and
$\emptyset_2$=outer diameter of the button body (mm).

The protrusion 50 is asymmetrical along its length, with a first surface 502 adjacent to the inner wall 40 or the button body 22 and a second surface 503 facing away from the first surface 61. A tip 504 is positioned between the first surface 502 and the second surface 503. Further, an angle of the first surface 502, A (degrees) with respect to the inner wall 40 or the button body 22 may be configured for insertion of the button 20 into the inner wall 40 from the proximal end 41 or the distal end 42 of the inner wall 40.

The protrusion 50 may be disposed between two elongate channels in the inner wall 40 or the button body 22 to define a cantilever snap fit. The elongate channels are not shown in the figures as cantilever snap fits are known to a person skilled in the mechanical arts and the skilled person would be able to configure the elongate channels within the inner wall 40 or the button body 22 in order to obtain a cantilever snap fit.

The protrusion 50 may be spaced from the inner wall 40 or the button body 22 for slidable movement of the button 20 within the inner wall 40 or engaged with the inner wall 40 or the button body 22 to guide a parallel movement of the button 20. Specifically, the first gap width, W3 may be defined as $$W3 \geq T1 \text{ (mm)}$$

wherein T1=depth of the protrusion relative to the inner wall or the button body (mm).

As shown in FIG. 9B, a ramp 70 may be disposed at a proximal end 24 of the button body 22 wherein the protrusion 50 is located at a distal end 42 of the inner wall 40 and spaced from the ramp 70 in a first position and abuts the ramp 70 in a second position to limit movement or a stroke of the button 20 so as to prevent the button 20 from being pushed further into the housing 10 once rupturing has occurred.

Figure 10A:
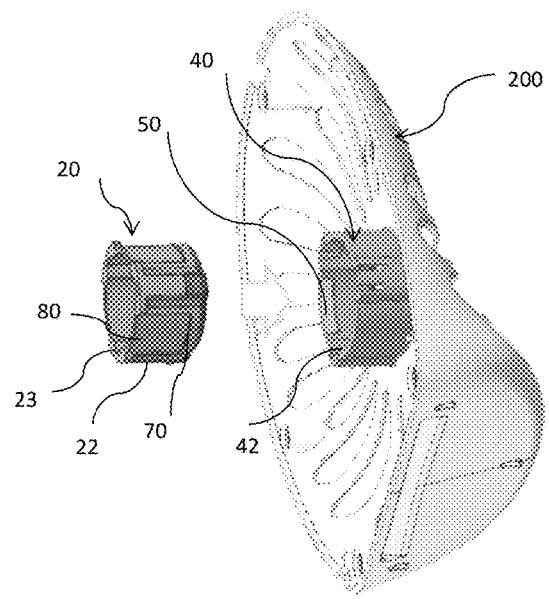
FIG. 10A is a side perspective view of a push button and a rear frame for a volatile composition dispenser.
Figure 10B:
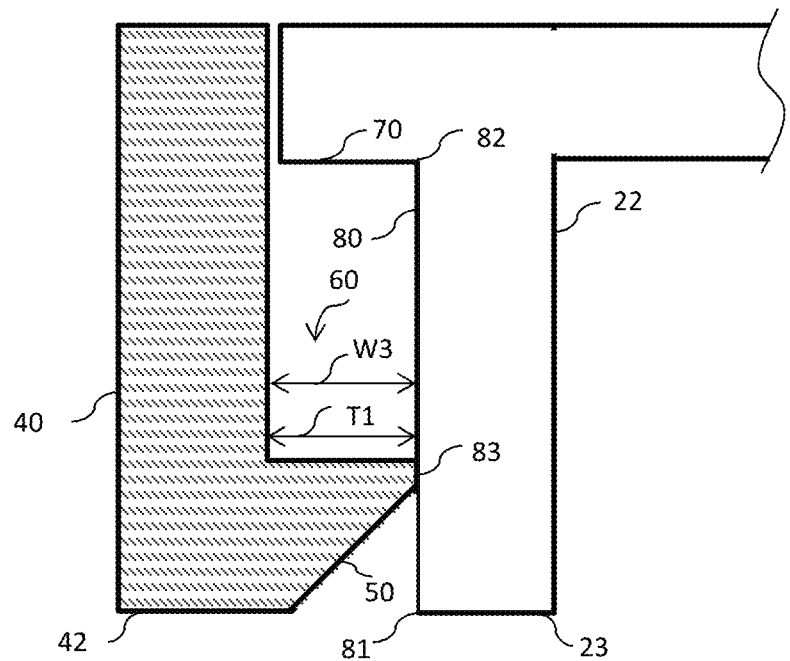
FIG. 10B is a schematic view of a push button within a rear frame.

One or more guide rails 80 may be disposed on the inner wall 40 or the button body 22. As shown in an embodiment as shown in FIGS. 10A and 10B, the button 20 comprises a guide rail 80 disposed on the button body 22 wherein the guide rail 80 is parallel to the inner wall 40 and extends from the distal end 23 of the button body 22 to a ramp 70 disposed on the button body 22. The protrusion 50 is disposed at the distal end 42 of the inner wall 40 of the rear frame 200. During assembly of the button 20 to the rear frame 200 as shown in FIG. 9B, the protrusion 50 engages the guide rail 80 to define a point of contact 83 for guiding the button 20. In an embodiment, the width, W3 may be equal to the depth T1 of the protrusion 50, i.e. W3=T1.

Figure 11:
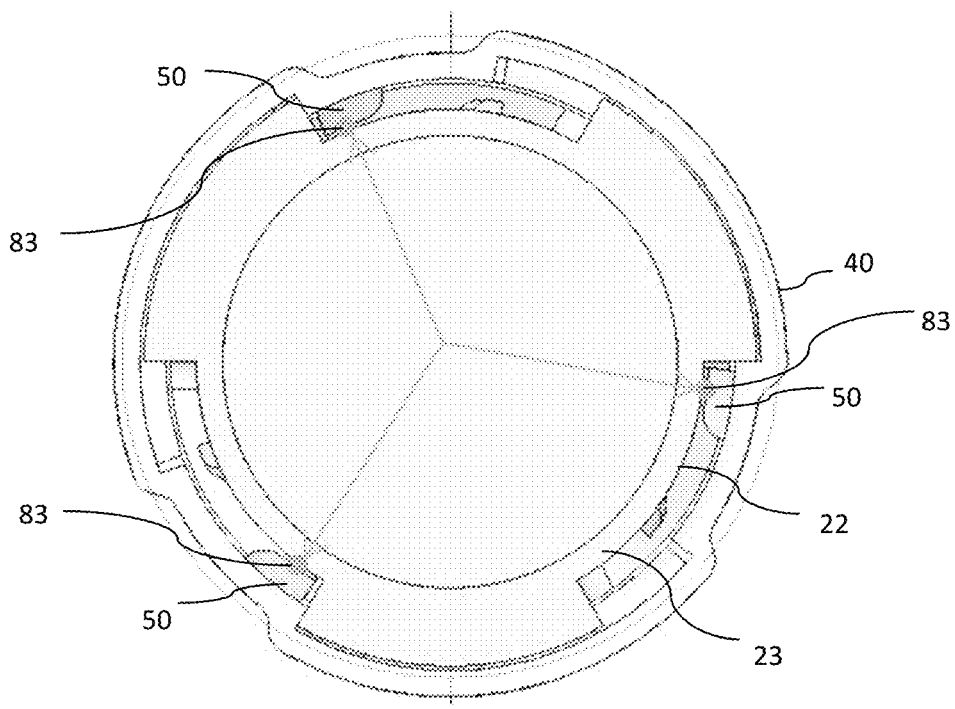
FIG. 11 is a different configuration of protrusions on a rear frame according to an embodiment.

Further, the guide rail 80 may comprise a first end 81 and a second end 82 wherein the ramp 70 is located at the second end 82 for abutting the protrusion 50 when the button 20 is pressed. FIG. 11 is a rear view of the button 20 within the rear frame 200 before activation, i.e. in a "at rest" position. Further, according to an embodiment as shown for example in FIG. 10, one or more protrusions 50 are spaced and located at the distal end 42 of the inner wall 40 and arranged to engage each of the guide rails 80 defining three points of contact 83 (also known as a three-point contact) between the button body 22 and the inner wall 40. The three-point contact defines a stable support plane for the button 20 when pressed in an off-center location on the top 21 so as to maintain parallel movement of the button 20 within the inner wall 40. In this way, an axial movement of the button 20 along the longitudinal axis 1000 relative to the rear frame 200 may be guided such that a distal end 23 of the button 20 is maintained within a plane parallel to the movable portion 234 of the rupture mechanism 34 (as shown in FIG. 7B). This minimizes tilting of the button 20 within the frame opening 201 thereby facilitating rupturing of the substrate 33 by all the rupture elements 37.

Figure 12:
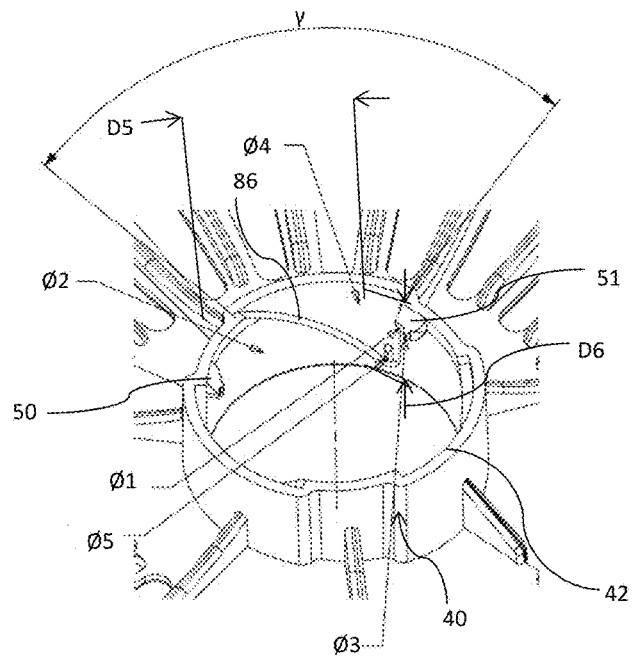
FIG. 12 is a rear perspective view of an inner wall in a rear frame for a volatile composition dispenser according to an embodiment.

FIG. 12 is a perspective view of the rear frame 200 of FIG. 3 (partially shown), FIG. 13A is a perspective view of an alternative of the button 20 and FIG. 13B is a bottom view of the button 20. One or more first and second protrusions 51, 52 may be located on each of the inner wall 40 and the button body 22. The first protrusion 51 or the second protrusion 52 may be generally elongate and extend in a direction parallel to the longitudinal axis 2000 of the frame opening 201. Each of the second protrusions 52 may comprise a length, L2 and each of the first protrusions 51 may comprise a length, L3. Each of the lengths L2 and L3 may be in the range of 7% to 20% of a length (L4) of the button 20. The guide rail 80 is a cam guide 80 and one or more second protrusions 52 are disposed on the cam guide 80 for engaging the one or more first protrusions 51 during rotation of the button 20. The first protrusions 51 are disposed at the distal end 42 of the inner wall 40 wherein the first protrusion 51 is aligned for engaging the cam guide 80 of the button body 22.

Referring to FIG. 13A, the cam guide 80 may comprise a plurality of first cam tracks 84 formed on the button body 22. The first cam tracks 84 are radially spaced apart on the button body 22 for engaging the first protrusions 51 on the distal end 42 of the inner wall 40. The cam guide 80 may further comprise a plurality of second cam tracks 85 intermediate the first cam tracks 84.

A cam angle α of the cam guide 80 may be configured to obtain a desired button stroke S (mm) and a rotation angle 3 of the button 20 about the longitudinal axis 1000 and/or the cylindrical axis 2000 (shown in FIG. 14B). The desired button stroke S may be a distance to be travelled by the button 20 along the longitudinal axis 1000 of the opening 201 in order to cause the rupture elements 37 of the rupture mechanism 34 to puncture the substrate 33.

By having the cam guide 80 and the first protrusion 51 cooperating to move the button 20 axially along and rotate about the longitudinal axis 1000 in a clockwise or an anti-clockwise direction, the top 21 of the button 20 may have different orientations with respect to the rear frame 200 as shown in FIG. 14A and FIG. 14B.

Specifically, the second cam tracks 85 extend radially outward from and spaced circumferentially on the button body 22 and arranged to engage mating cam track 86 formed on the inner wall 40 upon insertion of the button 20 in the inner wall 40. In an embodiment, each second cam track 85 and a mating cam track 86 may be configured to correspond in shape or profile to the first step 84 so as to define a continuous cam profile for rotation of the button 20 about the longitudinal axis 1000 and axial movement of the button 20 along the longitudinal axis 1000.

Further, the second cam tracks 85 and the mating cam tracks 86 may be configured to allow the button 20 to be arranged within the frame 200 at a height relative to the distal end 42 of the inner wall 40. The height may be varied so that upon assembly, the button 20 may be either flush with the periphery 207 of the opening 201 in the first position (as shown in FIG. 14A) or extending above the periphery 207 of the opening 201 in the first position (as shown in FIG. 15A). Further, indicia 90 may be disposed on the top 21 of the button 20 to provide a signal to a user of the dispenser 1. For example, referring to FIG. 14A, the indicia 90 may include a graphical representation like hands of a clock to show the button 20 in one orientation relative to the periphery of the opening in the first position and in a different orientation in the second position. Alternatively, referring to FIG. 15A, the indicia 90 may be a graphical symbol indicating a position for actuating the button 20 or activating the dispenser 1.

The inner wall 40, the first protrusion 51 and the frame 200 may be molded and form a unitary unit and may comprise plastic for ease of manufacturing. Similarly, the second protrusion 52, the cam guide 80 and the button 20 may also be molded and form a unitary plastic component. Alternatively, the button 20, and the frame 200 and the first and second protrusions 51, 52 may comprise sheet metal, such as spring steel, and may be stamped or milled to form a unitary metal component.

The volatile composition dispenser 1 may comprise a small form factor such as a form factor similar to a computer mouse so as for ergonomic fit in the hand of the user and ease of use. In embodiments, physical specifications of the inner wall 40, the button 20, the first and second protrusions 51, 52 and the cam guide 80 may be configured based on a specified button stroke S (millimeters) and/or a specified rotation angle $\beta$ (degrees) of the button 20 relative to the longitudinal axis 1000 as shown in FIG. 14B. Referring to FIGS. 12, 13A and 13B, Table 1 sets out physical specifications of the inner wall 40, the button 20, the protrusions 51, 52 and the guide rail 80 based on a button stroke S of 4.25 mm and a rotation angle $\beta$ of 42.5 degrees. A correlation between a button stroke S and a rotation angle $\beta$, $S/\beta$ may be 0.1 mm/degree. Therefore, it will be appreciated by a person skilled in the arts that the present invention is not limited to the physical specifications of Table 1. Specifically, the physical specifications may be modified based on a desired button stroke or button rotation angle using the correlation of $S/\beta = 0.1$ mm/degree. Further, the physical specifications may be modified by using a ratio of the cam angle, $\alpha$ to the button rotation angle, $\beta$ being 1.3.

TABLE 1

| Symbol as shown in FIGS. 12, 13A, 13B | Button Stroke S = 4.25 mm Button Rotation Angle, $\beta$ = 42.5 degrees |
|---|---|
| D1 (mm) | — |
| D2 (mm) | 4.63 |
| D3 (mm) | 8.9 |
| D4 (mm) | 9.95 |
| D5 (mm) | 13.85 |
| D6 (mm) | 6.6 |
| Diameter Ø1 (mm) | 14.75 |
| Diameter Ø2 (mm) | 16.27 |
| Diameter Ø3 (mm) | 14.36 |
| Diameter Ø4 (mm) | 17.76 |
| Diameter Ø5 (mm) | 17.15 |
| Diameter Ø6 (mm) | 16.03 |
| Diameter Ø7 (mm) | 14.41 |
| Diameter Ø8 (mm) | 17.34 |
| Diameter Ø9 (mm) | 15.53 |
| Angle $\alpha$ (degrees) | 55.25 |
| Angle $\gamma$ (degrees) | 77.07 |
| Angle $\Phi$ (degrees) | 55.17 |

The internal components of the cartridge 30 as shown in FIG. 3 may be characterized as follows. For example, dimensions of the container 32 may be configured to hold about 1 ml to about 50 ml of a liquid volatile composition. Alternatively, the reservoir 52 may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of a liquid volatile composition. Further, a shape of the container 32 may be configured to correspond to a shape of the opening 101 of the front cover 100. For example, the container 32 may define a substantially elliptical or oval shape and its width to length ratio may be about 1:2 to 1:2.5.

The rupturable substrate 33 can be made of any material that ruptures with applied force, with or without the presence of an element to aid in such rupture. Because the rupturable substrate 33 is intended to contain a volatile material while in storage, it may be made from any barrier material that prevents evaporation of the volatile material prior to its intended use. Such materials may be impermeable to vapors and liquids. Suitable barrier materials for the rupturable substrate 33 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 33. Such coated barrier films include metallized PET, metalized polypropylene, silica or alumina coated film may be used. Any barrier material, whether coated or uncoated, may be used alone and or in combination with other barrier materials.

The rupture element 37 can be injection, compression, or pressure molded using a polyolefin, such as polyethylene or polypropylene; polyester; or other plastics known to be suitable for molding. The rupture element 130 could also be made by thermoforming with a discrete cutting step to remove parts not wanted.

The membrane 39 may have an average pore size of about 0.01 to about 0.06 microns, alternatively from about 0.01 to about 0.05 microns, alternatively about 0.01 to about 0.04 microns, alternatively about 0.01 to about 0.03 microns, alternatively about 0.02 to about 0.04 microns, alternatively about 0.02 microns. Further, the membrane 39 may be filled with any suitable filler and plasticizer known in the art. Fillers may include finely divided silica, clays, zeolites, carbonates, charcoals, and mixtures thereof. The microporous membrane 39 may be filled with about 50% to about 80%, by total weight, of silica, alternatively about 60% to about 80%, alternatively about 70% to about 80%, alternatively about 70% to about 75%. A thickness of the membrane 39 may be about 0.01 mm to about 1 mm, alternatively between about 0.1 mm to 0.4 mm, alternatively about 0.15 mm to about 0.35 mm, alternatively about 0.25 mm.

Still further, an evaporative surface area of the microporous membrane 39 may be about 2 cm$^2$ to about 100 cm$^2$, alternatively about 2 cm$^2$ to about 25 cm$^2$, alternatively about 10 cm$^2$ to about 50 cm$^2$, alternatively about 10 cm$^2$ to about 45 cm$^2$, alternatively about 10 cm$^2$ to about 35 cm$^2$, alternatively about 15 cm$^2$ to about 40 cm$^2$, alternatively about 15 cm$^2$ to about 35 cm$^2$, alternatively about 20 cm$^2$ to about 35 cm$^2$, alternatively about 30 cm$^2$ to about 35 cm$^2$, alternatively about 35 cm$^2$. Accordingly, the rear frame 200 may be sized and shaped to fit the evaporative surface area of the membrane 39.

Suitable microporous membranes for the present invention include a microporous, ultra-high molecular weight polyethylene (UHMWPE) optionally filled with silica as described in U.S. Pat. No. 7,498,369. Such UHMWPE microporous membranes include Daramic™ V5, available from Daramic, Solupor™, available from DSM (Netherlands), and Teslin™, available from PPG Industries, and combinations thereof.

A volatile material or composition suitable for use in the cartridge 30 for a volatile composition dispenser 1 may be configured to condition, modify, or otherwise change the atmosphere and may include compositions suitable for the purposes of providing fragrances, air fresheners, deodorizers, odor eliminators, malodor counteractants, insecticides, insect repellants, medicinal substances, disinfectants, sanitizers, mood enhancers, and aromatherapy aids. A list of the suitable volatile materials is shown in Table 2 below.

TABLE 2

| Purpose | Volatile Material |
|---|---|
| Providing fragrances | Perfume oil, volatile essential oils, volatile organic compound, synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. Suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evernyl, and the like. |
| Neutralize malodors | Suitable malodor compositions include reactive aldehydes and ionones |

The composition may be formulated such that the composition comprises a volatile material mixture comprising about 10% to about 100%, by total weight, of volatile materials that each having a VP at 25° C. of less than about 0.01 torr, alternatively about 40% to about 100%, by total weight, of volatile materials each having a VP at 25° C. of less than about 0.1 torr, alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. The volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C. of about 0.1 torr to about 0.325 torr, and about 65% to about 100%, by total weight, of volatile materials each having a VP at 25° C. of about 0.035 torr to about 0.1 torr. One source for obtaining the saturation vapor pressure of a volatile material is EPI Suite™, version 4.0, available from U.S. Environmental Protection Agency.

An example is shown below:

A. A volatile composition dispenser (1) comprising:
   a housing (10) comprising a rear frame (200) having a frame opening (201);
   a push button (20) movably disposed within the frame opening (201); and a cartridge (30) aligned with the push button (20), the cartridge (30) comprising a container (32) having an orifice and containing a volatile composition (31), a rupturable substrate (33) sealably attached to and covering the orifice, and rupture elements (37) adjacent the rupturable substrate (33); and a resilient member (38) aligned with the push button (20) and the rupture elements (37) wherein upon receiving a pressure on the push button (20), said resilient member moves the rupture elements (37) into a first position in which the rupture elements (37) engage with the rupturable substrate (33) and wherein upon removing the pressure from the push button (20), said resilient member exerts a force on the push button (20) and moves the rupture elements (37) into a second position in which the rupture elements (37) are not engaged with the rupturable substrate (33).

B. A volatile composition dispenser (1) according to paragraph A, further comprising:
   an inner wall (40) having a proximal end (41) at a periphery (207) of the frame opening (201) and a distal end (42) extending into the opening;
   a gap (60) between a button body (22) of the push button (20) and the inner wall (40); and
   a protrusion (50) disposed at the distal end (41, 23) of the inner wall (40) or the button body (22), wherein the protrusion (50) is arranged within the gap (60).

C. A volatile composition dispenser (1) according to paragraph B, wherein the protrusion (50) comprises a first surface (502) adjacent to the other of the inner wall (40) or the button body (22), wherein an angle of the first surface, A with respect to the inner wall (40) or the button body (22) is configured for insertion of the button (20) into the inner wall (40) from the proximal end (41) or the distal end (42) of the inner wall (40).

D. A volatile composition dispenser (1) according to paragraph B, wherein the protrusion (50) is disposed between two elongate channels in the inner wall (40) or the button body (22) to define a cantilever snap fit.

E. A volatile composition dispenser (1) according to paragraph B, wherein the inner wall (40) and the button body (22) are coaxial and are substantially cylindrical, the inner wall (40) comprising an inner diameter, $\varnothing_1$, and the button body (22) comprises an outer diameter, $\varnothing_2$, wherein a width, W of the gap (50) is defined as $W=(\varnothing_1-\varnothing_2)/2$, millimeters (mm).

F. A volatile composition dispenser (1) according to paragraph C, further comprising a ramp (70) disposed on the other of the inner wall (40) or the button body (22) wherein the protrusion (50) is spaced from the ramp (70) in a first position and abuts the ramp (70) in a second position to limit movement of the button (20) when pushed.

G. A volatile composition dispenser (1) according to paragraph F, further comprising a guide rail (80) disposed on the other of the inner wall (40) or the button body (22); the guide rail (80) comprises a first end (81) and a second end (82), wherein the ramp (70) is located at the first end (81) or the second end (82).

H. A volatile composition dispenser (1) according to paragraph G, wherein the protrusion (50) is configured to engage the guide rail (80).

I. A volatile composition dispenser (1) according to paragraph H, wherein the guide rail (80) is parallel to the inner wall (40) or the button body (22).

J. A volatile composition dispenser (1) according to paragraph H, wherein the push button (20) is axially movable along and rotatable about a longitudinal axis (1000) at a rotation angle, β (degrees) in response to a force on the push button (20), wherein the guide rail (80) is a cam guide (80) comprising a cam angle, α (degrees) relative to a cylindrical axis of the inner wall (40) or the button body (22), wherein α>β.

K. A volatile composition dispenser (1) according to paragraph J, wherein a ratio of the cam angle, α to the button rotation angle, β is 1.3.

L. A volatile composition dispenser (1) according to paragraph K, wherein the cam guide (80) is discontinuous and comprises a plurality of first cam tracks (84) on the inner wall or the button body, wherein the plurality of first cam tracks (84) are radially spaced apart on the inner wall or the button body and engage protrusions (51, 52) on the other of the inner wall or button body.

M. A volatile composition dispenser (1) according to paragraph L, wherein the cam guide (80) comprises second cam tracks (85) intermediate the first cam tracks (84), wherein the second cam tracks (85) engages mating cam tracks (86) on the other of the inner wall or button body.

N. A volatile composition dispenser (1) according to paragraph A, wherein the cartridge (30) comprises a rupture mechanism (34) comprising
 a wall (341) comprising a groove (342) extending circumferentially within the wall (341) to define a center portion (343) inside the groove (341) and an outer portion (344) outside the groove (342), the center portion (343) comprising a substantially planar first surface (345); wherein the resilient member (38) is a spring attaching the outer portion (344) to the center portion (343) and the rupture elements (37) are arranged within the rupture mechanism (34).

O. A volatile composition dispenser (1) according to paragraph N, wherein the resilient member (38) comprises a first arm (382) attached to the outer portion (344), a second arm (383) attached to the center portion (344), and a elongate channel member (384) extending between the first and second arms (382, 383), the elongate channel member (384) comprising a channel width (W1) substantially parallel to the first surface (345) of the center portion (343).

P. A volatile composition dispenser (1) as claimed in paragraph O, wherein the elongate channel member (384) comprises a channel length (L) greater than the channel width (W1).

Q. A volatile composition dispenser (1) as claimed in paragraph O, wherein the elongate channel member (384) comprises two side beams (385) and a bottom beam (386) arranged to form a substantially U-shape.

R. A volatile composition dispenser (1) as claimed in paragraph A, wherein the rear frame (200) and the protrusion (50) form a unitary unit.

S. A volatile composition dispenser (1) as claimed in paragraph A, wherein the button (20), the rear frame (200) and the protrusion (50) comprise plastic.

T. A method of assembling a volatile composition dispenser, the method comprising:
 providing a housing comprising a rear frame having a frame opening and a longitudinal axis (1000) disposed centrally within said opening;
 inserting a push button in the frame opening, wherein the button is movable within the frame opening;
 aligning a cartridge with the push button, wherein the cartridge comprises a container (32) having an orifice and containing a volatile composition (31), a rupturable substrate (33) sealably attached to and covering the orifice, and rupture elements (37) adjacent the rupturable substrate (33); and a resilient member (38) aligned with the push button (20) and the rupture elements (37) to: upon receiving a pressure on the push button (20), store energy and move the rupture elements (37) into a first position in which the rupture elements (37) engages with the rupturable substrate (33); and upon removing the pressure from the push button (20), to exert a force on the push button (20) and move the rupture elements (37) into a second position in which the rupture elements (37) are not engaged with the rupturable substrate (33); and attaching the cartridge to the rear frame.

U. A method of assembling according to paragraph T, wherein inserting the button comprises:
 providing an inner wall (40) having a proximal end (41) at a periphery (207) of the frame opening (201) and a distal end (42) extending into the opening (201) and engaging a protrusion (50) located at the distal end (42) of the inner wall (40) with the button body (22).

V. A method of assembling according to paragraph U, wherein the button body comprises a guide rail, wherein the protrusion is engaged with the guide rail.

W. A method of assembling according to paragraph T, wherein the attaching the cartridge (30) to the rear frame (200) comprises attaching a front cover (100) to the rear frame (200).

X. A method of assembling according to paragraph W, wherein the front cover (100) is attached to the rear frame (200) through a mechanical attachment means or a chemical attachment means.

Y. A method of activating a push button in a volatile composition dispenser, the method comprising:
 providing a housing (10) comprising a rear frame (200) having a frame opening (201) and a cartridge (30) disposed within the housing (10), the cartridge (30) comprising a container (32) having an orifice and containing a volatile composition (31), a rupturable substrate (33) sealably attached to and covering the orifice, and rupture elements (37) adjacent the rupturable substrate (33); and a resilient member (38) aligned with the rupture elements (37);
 applying a pressure to a push button movable within the frame opening to store energy in the resilient member (38) and move the rupture elements (37) into a first position in which the rupture elements (37) engages with the rupturable substrate (33); and
 removing the pressure from the push button (20) to allow the resilient member (38) to exert a force on the push button (20) and move the rupture elements (37) into a second position in which the rupture elements (37) are not engaged with the rupturable substrate (33).

Various embodiments will now be described to provide an overall understanding of the principles of the structure, function, manufacture, and use of the apparatuses and methods disclosed herein. One or more examples of these embodiments are illustrated in the accompanying drawings. Those of ordinary skill in the art will understand that the apparatuses and methods specifically described herein and illustrated in the accompanying drawings are non-limiting example embodiments and that the scope of the various embodiments of the present disclosure are defined solely by the claims. The features illustrated or described in connection with one example embodiment may be combined with the features of other example embodiments. Such modifications and variations are intended to be included within the scope of the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising:
   a housing comprising a rear frame having a frame opening;
   an inner wall having a proximal end at a periphery of the frame opening and a distal end extending into the opening;
   a push button movably disposed within the frame opening;
   a gap between a button body of the push button and the inner wall;
   a protrusion disposed at the distal end of the inner wall or the button body, wherein the protrusion is arranged within the gap;
   a ramp disposed on the other of the inner wall or the button body wherein the protrusion is spaced from the ramp in a first position and abuts the ramp in a second position to limit movement of the button when pushed;
   a cam guide disposed on the other of the inner wall or the button body, wherein the protrusion engages with the cam guide, and wherein the push button is axially movable along and rotatable about a longitudinal axis at a rotation angle, $\beta$ (degrees) in response to a force on the push button, wherein the cam guide comprises a cam angle, $\alpha$ (degrees) relative to a cylindrical axis of the inner wall or the button body, wherein $\alpha > \beta$; and
   a cartridge aligned with the push button, the cartridge comprising a container having an orifice and containing a volatile composition, a rupturable substrate sealably attached to and covering the orifice, and rupture elements adjacent the rupturable substrate, the rupture elements each comprising a tip for puncturing the rupturable substrate; and a resilient member aligned with the push button and the rupture elements to:
      upon receiving a pressure on the push button, store energy and move the rupture elements into a first position in which the rupture elements engage with the rupturable substrate; and
      upon removing the pressure from the push button, to exert a force on the push button and move the rupture elements into a second position in which the rupture elements are not engaged with the rupturable substrate.

2. A volatile composition dispenser according to claim 1, wherein the protrusion comprises a first surface adjacent to the other of the inner wall or the button body, wherein an angle of the first surface, A with respect to the inner wall or the button body is configured for insertion of the button into the inner wall from the proximal end or the distal end of the inner wall.

3. A volatile composition dispenser according to claim 1, wherein the inner wall and the button body are coaxial and are substantially cylindrical, the inner wall comprising an inner diameter, $\varnothing_1$, and the button body comprises an outer diameter, $\varnothing_2$, wherein a width, W of the gap is defined as $W=(\varnothing_1-\varnothing_2)/2$, millimeters (mm).

4. A volatile composition dispenser according to claim 1, wherein a ratio of the cam angle, a to the button rotation angle, $\beta$ is 1.3.

5. A volatile composition dispenser according to claim 4, wherein the cam guide is discontinuous and comprises a plurality of first cam tracks, wherein the plurality of first cam tracks are radially spaced apart on the other of the inner wall or the button body and wherein the protrusion comprises a plurality of protrusions each of which engages a respective one of the plurality of first cam tracks.

6. A volatile composition dispenser according to claim 5, wherein the cam guide comprises second cam tracks intermediate the plurality of first cam tracks, and mating cam tracks, wherein the second cam tracks engage the mating cam tracks on the other of the inner wall or button body.

7. A volatile composition dispenser according to claim 1, wherein the cartridge comprises a rupture mechanism comprising
   a wall comprising a groove extending circumferentially within the wall to define a center portion inside the groove and an outer portion outside the groove, the center portion comprising a substantially planar first surface;
   wherein the resilient member is a spring attaching the outer portion to the center portion and the rupture elements are arranged within the rupture mechanism.

8. A volatile composition dispenser according to claim 7, wherein the resilient member comprises a first arm attached to the outer portion, a second arm attached to the center portion, and an elongate channel member extending between the first and second arms, the elongate channel member comprising a channel width substantially parallel to the first surface of the center portion.

9. A volatile composition dispenser as claimed in claim 8, wherein the elongate channel member comprises a channel length greater than the channel width.

10. A volatile composition dispenser as claimed in claim 8, wherein the elongate channel member comprises two side beams and a bottom beam arranged to form a substantially U-shape.

11. A volatile composition dispenser as claimed in claim 1, wherein the rear frame and the protrusion form a unitary unit.

\* \* \* \* \*